US009655628B2

(12) United States Patent
Boyer et al.

(10) Patent No.: US 9,655,628 B2
(45) Date of Patent: May 23, 2017

(54) REDUCED INVASIVITY FIXATION SYSTEM FOR TRACKERS IN COMPUTER ASSISTED SURGERY

(75) Inventors: Anthony Boyer, Echirolles (FR); Stéphane Lavallee, St. Martin d'Uriage (FR)

(73) Assignee: BLUE ORTHO, La Tronche (FR)

( * ) Notice: Subject to any disclaimer, the term of this patent is extended or adjusted under 35 U.S.C. 154(b) by 0 days.

(21) Appl. No.: 13/318,815

(22) PCT Filed: May 4, 2010

(86) PCT No.: PCT/IB2010/001804
§ 371 (c)(1),
(2), (4) Date: Jan. 18, 2012

(87) PCT Pub. No.: WO2010/128409
PCT Pub. Date: Nov. 11, 2010

(65) Prior Publication Data
US 2012/0109228 A1    May 3, 2012

Related U.S. Application Data

(60) Provisional application No. 61/175,865, filed on May 6, 2009.

(51) Int. Cl.
*A61F 2/46* (2006.01)
*A61B 17/15* (2006.01)
(Continued)

(52) U.S. Cl.
CPC ............ *A61B 17/154* (2013.01); *A61B 34/20* (2016.02); *A61B 2090/3983* (2016.02)

(58) Field of Classification Search
CPC ................ A61B 17/155; A61B 17/157; A61B 2019/5287; A61B 19/5244; A61B 17/15; A61B 17/154; A61B 17/158
(Continued)

(56) References Cited

U.S. PATENT DOCUMENTS

| 4,457,307 A | 7/1984 | Stillwell |
| 4,681,843 A | 7/1987 | Egerer et al. |
| | (Continued) | |

FOREIGN PATENT DOCUMENTS

| DE | 100 29 737 | 5/2003 |
| EP | 0 728 446 | 8/1996 |
| | (Continued) | |

OTHER PUBLICATIONS

International Search Report and Written Opinion Based on PCT/IB2010/001804 mailed Feb. 8, 2011.
(Continued)

*Primary Examiner* — Si Ming Ku
(74) *Attorney, Agent, or Firm* — Blakely Sokoloff Taylor & Zafman LLP (57) ABSTRACT

The invention relates to a surgical navigation device, for the purpose of adjusting a cutting plane to a desired position with respect to a bone of a patient, the device comprising:
a fixed part (7) rigidly attached to the bone (18, 19), the fixed part comprising fixation means to rigidly attach a tracker thereto;
a mobile part (5) adjustable with respect to the fixed part (7), including fixation means to rigidly attach a tracker thereto, and including a cutting slot (6) in which a saw blade can be inserted to perform cut;
a fixed tracker (9) rigidly attached to the fixed part (7);
a mobile tracker (1) attached to the mobile part (5).
The invention also concerns a method for adjusting a cutting plane of a surgical device to a desired position with respect to a bone of a patient.

7 Claims, 4 Drawing Sheets

(51) Int. Cl.
*A61B 90/00* (2016.01)
*A61B 34/20* (2016.01)

(58) Field of Classification Search
USPC .................................. 606/86 R, 87–90, 102
See application file for complete search history.

(56) References Cited

U.S. PATENT DOCUMENTS

| | | | |
|---|---|---|---|
| 4,706,665 | A | 11/1987 | Gouda |
| 5,251,127 | A | 10/1993 | Raab |
| 5,305,203 | A | 4/1994 | Raab |
| 5,601,563 | A * | 2/1997 | Burke .................. A61B 17/154 606/62 |
| 5,682,886 | A | 11/1997 | Delp et al. |
| 5,806,518 | A | 9/1998 | Mittelstadt |
| 5,871,018 | A | 2/1999 | Delp et al. |
| 5,995,738 | A | 11/1999 | Digioia, III et al. |
| 6,340,363 | B1 | 1/2002 | Bolger et al. |
| 6,351,659 | B1 | 2/2002 | Vilsmeier |
| 6,450,978 | B1 | 9/2002 | Brosseau et al. |
| 6,533,737 | B1 | 3/2003 | Brosseau et al. |
| 6,551,325 | B2 | 4/2003 | Neubauer et al. |
| 6,685,711 | B2 | 2/2004 | Axelson, Jr. et al. |
| 6,712,824 | B2 | 3/2004 | Millard et al. |
| 6,916,325 | B2 * | 7/2005 | Kana et al. ...................... 606/89 |
| 6,991,655 | B2 | 1/2006 | Iversen |
| 7,029,477 | B2 * | 4/2006 | Grimm .......................... 606/88 |
| 7,309,339 | B2 * | 12/2007 | Cusick .................. A61B 17/154 606/88 |
| 7,419,492 | B2 | 9/2008 | Yoon et al. |
| 2002/0010465 | A1 | 1/2002 | Koo et al. |
| 2002/0133160 | A1 | 9/2002 | Axelson, Jr. et al. |
| 2003/0181800 | A1 | 9/2003 | Bonutti |
| 2004/0044295 | A1 | 3/2004 | Reinert et al. |
| 2004/0092944 | A1 | 5/2004 | Penenberg |
| 2004/0097952 | A1 | 5/2004 | Sarin et al. |
| 2004/0143340 | A1 | 7/2004 | Tuma et al. |
| 2004/0230199 | A1 | 11/2004 | Jansen et al. |
| 2004/0243148 | A1 | 12/2004 | Wasielewski |
| 2004/0254584 | A1 | 12/2004 | Sarin et al. |
| 2005/0010299 | A1 | 1/2005 | Disilvestro |
| 2005/0010301 | A1 | 1/2005 | Disilvestro |
| 2005/0021044 | A1 | 1/2005 | Stone et al. |
| 2005/0065617 | A1 | 3/2005 | Moctezuma De La Barrera et al. |
| 2005/0119661 | A1 | 6/2005 | Hodgson et al. |
| 2005/0203536 | A1 | 9/2005 | Laffargue et al. |
| 2005/0234468 | A1 | 10/2005 | Carson |
| 2006/0195111 | A1 | 8/2006 | Couture |
| 2006/0200161 | A1 | 9/2006 | Plaskos et al. |
| 2006/0217733 | A1 * | 9/2006 | Plassky et al. .................. 606/87 |
| 2006/0235290 | A1 | 10/2006 | Gabriel et al. |
| 2007/0010258 | A1 | 1/2007 | Landschaft et al. |
| 2007/0038223 | A1 | 2/2007 | Marquart et al. |
| 2007/0055289 | A1 | 3/2007 | Scouten et al. |
| 2007/0055389 | A1 | 3/2007 | Harwood |
| 2007/0066917 | A1 | 3/2007 | Hodorek et al. |
| 2007/0118139 | A1 * | 5/2007 | Cuellar .................. A61F 5/058 606/87 |
| 2007/0162142 | A1 | 7/2007 | Stone |
| 2007/0179626 | A1 | 8/2007 | De La Barrera et al. |
| 2007/0219561 | A1 | 9/2007 | Lavallee et al. |
| 2007/0244488 | A1 | 10/2007 | Metzger et al. |
| 2008/0009952 | A1 | 1/2008 | Hodge |
| 2008/0065085 | A1 * | 3/2008 | Couture et al. .................. 606/87 |
| 2008/0071195 | A1 | 3/2008 | Cuellar et al. |
| 2008/0140081 | A1 * | 6/2008 | Heavener .............. A61B 17/155 606/87 |
| 2008/0146969 | A1 | 6/2008 | Kurtz |
| 2008/0172054 | A1 * | 7/2008 | Claypool .............. A61B 17/157 606/87 |
| 2008/0214960 | A1 | 9/2008 | Hodgson et al. |
| 2009/0005783 | A1 | 1/2009 | Gotte et al. |

FOREIGN PATENT DOCUMENTS

| | | |
|---|---|---|
| EP | 1 226 778 | 7/2002 |
| EP | 1 245 193 | 10/2002 |
| EP | 1 430 842 | 6/2004 |
| EP | 1 444 957 | 8/2004 |
| EP | 1 574 170 | 9/2005 |
| EP | 1 665 992 | 6/2006 |
| EP | 1 669 033 | 6/2006 |
| EP | 1 679 047 | 7/2006 |
| EP | 1 707 159 | 10/2006 |
| EP | 2 042 110 | 4/2009 |
| FR | 2 856 268 | 12/2004 |
| WO | 01/78015 | 10/2001 |
| WO | 02/37935 | 5/2002 |
| WO | 03/009768 | 2/2003 |
| WO | 03/079940 | 10/2003 |
| WO | 2009/105479 | 8/2009 |
| WO | 2009/127404 | 10/2009 |
| WO | 2010/125474 | 11/2010 |

OTHER PUBLICATIONS

International Preliminary Report on Patentability and Written Opinion Based on International Application No. PCT/EP2009/063930 Issued Apr. 26, 2011.

Kosmopoulos, Ph.D. et al.; "Pedicle Screw Placement Accuracy: A Meta-Analysis", Spine; 2007; vol. 32, No. 3; pp. E111-E120; Lippincott Williams & Wilkins, Inc.

Grützner et al.; "Klinische Studie Zur Registrierungsfreien 3D-Navigation Mit Dem Mobilen C-Bogen Siremobil ISO-C 3D"; Electromedica; 2003; vol. 71; No. 1; pp. 58-67; Lippincott Williams & Wilkins, Inc.

Schaeren et al; "Effektive In-Vivo-Strahlendosis Bei Bildwandlerkrontollierter Pedikelinstrumentation Vs. CT-Basierter Navigation"; Orthopade; Apr. 2002; vol. 31, No. 4; pp. 392-396; Springer-Verlag.

Laine et al.; "Accuracy of Pedicle Screw Insertion With and Without Computer Assistance: A Randomised Controlled Clinical Study in 100 Consecutive Patients"; European Spine Journal; 2000; vol. 9; No. 3; pp. 235-240; Springer-Verlag.

Sukovich et al; "Miniature Robotic Guidance for Pedicle Screw Placement in Posterior Spinal Fusion: Early Clinical Experience With the SpineAssist"; International Journal of Medical Robotics and Computer Assisted Surgeryr+; Jun. 2006; vol. 2, No. 2; pp. 114-122; John Wiley & Sons, Ltd.

Wendl et al; "ISO-C3D-Gestutzte Navigierte Implantation Von Pedikiel-Schrauben an BWS Und LWS"; Unfallchirurg; Nov. 2003; vol. 106; No. 11; pp. 907-913; Springer-Verlag.

Susil et al.; "A Single Image Registration Method for CT Guided Interventions" MICCAI '99; 1999; LNCS 1679; pp. 798-808; Springer-Verlag Berlin Heidelberg.

Amiot et al.; "Comparative Results Between Conventional and Computer-Assisted Pedicle Screw Installation in the Thoracic, Lumbar, and Sacral Spine"; Spine; 2000; vol. 25; No. 5; pp. 606-614; Lippincott Williams & Wilkins, Inc.

Hamadeh et al.; "Automated 3-Dimensional Computed Tomographic and Fluoroscopic Image Registration"; 1998; Computer Aided Surgery; Biomedical Paper; vol. 3; No. 1; pp. 11-19; Wiley-Liss, Inc.

Horn; "Closed-Form Solution of Absolute Orientation Using Unit Quaternions"; 1987; Journal of the Optical Society of America A; 1987; vol. 4; p. 629; Optical Society of America.

Merloz et al.; "Computer-Assisted Spine Surgery"; 1998; Computer Aided Surgery; vol. 3; pp. 297-305; Wiley-Liss, Inc.

Lazovic; "Cup and Stem Navigation With the Orthopilot System, In Navigation and Mis in Orthopaedic Surgery"; 2007; Ed. Stiehl JB; Konermann WH, Haaker RG, Digioia AM; Springer Medizin Verlag; Heidelberg; pp. 372-378.

Perlick et al.; "Cup and Stem Navigated With the Vector Vision System. In Navigation and Mis in Orthopaedic Surgery"; 2007; Ed. Stiehl JB, Konermann WH, Haaker RG, Digioia AM; Springer Medizin Verlag, Heidelberg, pp. 378-384.

(56) References Cited

OTHER PUBLICATIONS

International Search Report and Written Opinion Based on PCT/IB2010/001807 Mailed Oct. 19, 2010.
Radermacher et al.; "Computer Assisted Orthopedic Surgery by Means of Individual Templates Aspects and Analysis of Potential Applications"; First International Symposiumon Medical Robotics and Computer Assisted Surgery; 1994; pp. 42-48.
PhD Thesis of Markus Fleute; "Non-Rigid 3D/3D Registration of Sparse Scattered Point Data With a Statistical Shape Model and Its Application to Computer Assisted ACL Surgery"; Universite Joseph Fourier; Grenoblem, France; 1999; Chapter 6.
Nogler; "Navigated Minimal Invasive Total Hip Arthroplasty"; Orthopaedic Surgery; Surg Tech. Int.; 2004; vol. 12; 2PP. 59-262.
Lewinnek et al.; "Dislocations After Total Hip-Replacement Arthroplasties"; J Bone and Joint Surg AM; Mar. 1978 ; vol. 60 A; No. 2; pp. 217-220; The Journal of Bone and Joint Surgery, Incorporated.
Stindel et al.; "Detection of the Center of the Hip Joint in Computer-Assisted Surgery : An Evolution Study of the Surgetic Algorithm"; Computer Aided Surgery; 2005; vol. 10; No. 3; pp. 133-139; Taylor & Francis Group.
Sarin et al.; "Accurate Femur Repostioning Is Critical During Intraoperative Total Hip Arthroplasty Leg Length and Offset Assesment"; J Arthroplasty; 2005; vol. 20; No. 7; pp. 887-891; Elsevier Inc.
Widmer et al.; "Compliant Positioning of Total Hip Components for Optimal Range of Motion"; J Orthop Res; 2004; vol. 22; pp. 815-821; Elsevier.
Duwelius et al.; "Minimally Invasive Total Hip Arthorplasty: An Overview of the Results"; AAOS Instructional Course Lectures; 2008; vol. 57; pp. 215-222.
D'Lima et al.; "The Effect of Oreintation of the Acetabular and Femoral Components on the Range of Motion of the Hip at Different Head-Neck Ratios"; The Journal of Bone and Joint Surgery—American; J Bone and Joint Surg; Mar. 2000; vol. 82 A; No. 3; pp. 315-321.
Wixson; "Computer-Assisted Total Hip Navigation"; AAOS Instructional Course Lectures; 2008; vol. 57; pp. 707-720.
Schmerwitz; "Total Hip Arthroplasty: First Experiences With Pinless THA Software to Determine Leg Length and Offset"; Orthopaedics; 2007; vol. 30; pp. S124-S126.
Della Valle et al.; "Preoperative Planning for Primary Total Hip Arthorplasty"; J American Academy of Orthopaedic Surgeons; 2005; vol. 13; No. 7; pp. 455-462; American Academy of Orthopaedic Surgeons.
Soong et al.; "Dislocation After Total Hip Arthroplasty"; J American Academy of Orthopaedic Surgeons; 2004; vol. 12; pp. 314-321.
Barrack; "Dislocation After Total Hip Arthroplasty : Implant Design and Orientation"; J American Academy of Orthopaedic Surgeons; Mar./Apr. 2003; vol. 11; No. 2; pp. 89-99; American Academy of Orthopaedic Surgeons.
Clark RT al.; "Leg-Length Discrepancy After Total Hip Arthroplasty"; J American Academy of Orthopaedic Surgeons; 2006; vol. 14; pp. 38-45.; American Academy of Orthopaedic Surgeons.
Haaker et al.; "Comparison of Conventional Versus Computer-Navigated Acetabular Component Insertion"; The Journal of Arthroplasty; vol. 00 No. 0; 2005; pp. 1-8; Elsevier Inc.
Buckup et al.; "Minimally Invasive Implantation and Computer Navigation for a Unicondylar Knee System"; MIS; Extract From Ortho Supersite; Hawaii's Big Island Jan. 11-14, 2009.
Stiehl et al.; "Accuracy of Acetabular Component Positioning With a Fluoroscopically Referenced Caos System"; Computer Aided Surgery; Sep./Nov. 2005; 10(5/6); pp. 321-327; Taylor & Francis.
Stiehl et al.; "Validation and Metrology in Caos"; Extracted on Dec. 9, 2006; Chapter 9; pp. 68-78.
Radermacher et al.; "Computer Integrated Advanced Orthopedics (CIAO)"; ESME; Stuttgart, Germany; 1993.
Radermacher ER al.; "Computer Assisted Matching of Planning and Execution in Orthopedic Surgery"; 1993; IEEE EMBS; San Diego; U.S.A.
Eckhoff et al.; "Three-Dimensional Mechanics, Kinematics, and Morphology of the Knee Viewed in Virtual Reality"; JBJS; 2005; vol. 87; pp. 71-80; The Journal of Bone and Joint Surgery.
Coughlin et al.; "Tibial Axis and Patellar Position Relative to the Femoral Epicondylar Axis During Squatting"; Journal of Arthroplasty; Dec. 2003; vol. 18; No. 8; pp. 1048-1055.
Murphy, S.B.; "Alumina Ceramic—Ceramic Total Hip Arthroplasty Using Computer-Assisted Surgical Navigation and a New Minimally Invasive Technique"; Advanced Ceramic Applications and New Projects; $9^{th}$ Symposium 2.5; 2004; pp. 61-69.
Columbia-St. Mary's Stiehl News: Extract of Website Columbia St. Mary's Milwaukee Wisconsin—Columbia St. Mary's Launches New Surgical Navigation for Orthopaedic Surgery, [online], [retrieved on Oct. 5, 2008]. Retrieved from the Internet <URL: http://www.columbia-stmarys.org/NewsPressReleases. asp?PageID=WTN000096>.
PreGrant Publication Database Search Results—List of Results of Search in PGPUB Production Database for: "Computer Assisted" and "Hip", [online], [retrieved on Oct. 5, 2008]. Retrieved from the Internet.
Stiehl et al.; "Computer Assisted Surgery: Principles"; Part V; Chapter 38; Technology; 2005; pp. 241-246.
Stiehl et al.; "Validation of Imageless Total Hip Navigation"; Part IV A; Chapter 42; Navigation: Total Hip Arthroplasty; 2007; pp. 334-338.

* cited by examiner

REDUCED INVASIVITY FIXATION SYSTEM FOR TRACKERS IN COMPUTER ASSISTED SURGERY

CROSS REFERENCE TO RELATED APPLICATIONS

This application is a §371 National Stage Application of PCT/IB2010/001804, filed May 4, 2010, which claims priority to U.S. Provisional Application No. 61/175,865, filed May 6, 2009.

BACKGROUND OF THE INVENTION

Field of the Invention

The present invention relates to a device that reduces the invasivity of tracker fixation compared to conventional tracker fixations in surgical navigation. The scope of the invention is limited to the navigation of bone cuts in orthopaedic surgery, such as for instance total knee arthroplasty, uni knee arthroplasty, and knee revision procedures.

Description of Related Art

It is known that some navigation systems are tracking instrument position during their position adjustment.

It is known that some cutting blocks are tracked in real-time by a navigation system for bone cuts and in particular for total knee replacement procedures.

It is known that some cutting blocks have mechanism such that the cutting plane position can be adjusted to reach precisely a target position.

In a traditional knee arthroplasty procedure, the tibial and femoral distal cutting blocks are fixed to the bone by screws or pins. Existing navigation systems require additional fixations to attach a tracker on the tibia and a tracker on the femur. This is a major drawback of navigation systems. Surgeons and patients are more and more reluctant to make additional holes into the bone for navigation purpose, because it creates additional scars, it increases the fragility of the bone and it adds time to the procedure.

The goal of the invention is to propose a device that requires only one fixation system to the bone for holding the cutting block, the cutting block tracker, and the bone tracker in order to suppress the additional fixation of bone trackers.

SUMMARY

The tracking technology of trackers and navigation systems is independent of the invention, provided that the trackers are tracked in real-time by the navigation system. It includes, but is not limited to, optical active technology, with active infrared Light Emitting Diodes (LEDs) on trackers, optical passive technology (with passive retro-reflective markers on trackers), mechanical passive arms with encoders, radio-frequency measurements, gyro meters and accelerometers or magnetic technology. Those tracking technologies are known as prior art of navigation systems for surgery.

An object of the invention is a surgical navigation device, for the purpose of adjusting a cutting plane to a desired position with respect to a bone of a patient, the device comprising:
  a fixed part which is rigidly attached to the bone, the fixed part comprising fixation means to rigidly attach a tracker thereto;
  a mobile part that is adjustable with respect to the fixed part, including fixation means to rigidly attach a tracker thereto, and including a cutting slot in which a saw blade can be inserted to perform cut;
  a fixed tracker that is rigidly attached to the fixed part;
  a mobile tracker that is attached to the mobile part.

This surgical navigation device allows reducing the invasivity of tracker fixation to the bone, by suppressing the use of an additional fixation to attach a tracker to the bone. The device of the invention here takes the advantage of the existing fixation system of the cutting block to the bone, in order to use a single fixation system for both cutting block and bone tracker.

Preferably, the mobile part is adjusted with respect to the fixed part using a parallel architecture made of three screws.

According to a preferred embodiment, the fixed part comprises a bone fixation through which it is attached to the bone and the fixed tracker is attached to said bone fixation.

The device advantageously comprises a template rigidly attached to the fixed part, and the template comprises landmarks corresponding to anatomical landmarks of the bone that help for initial positioning.

Preferably, the fixed part also comprises a rod for manipulating the device and indicating its gross alignment with the bone axis.

Another object of the invention is a method for adjusting a cutting plane of a surgical device to a desired position with respect to a bone of a patient, the device comprising a fixed part which is rigidly attached to the bone and a mobile part that is adjustable with respect to the fixed part, including a cutting slot in which a saw blade can be inserted to perform cut, said method comprising the following steps:
attaching a fixed tracker to the fixed part;
attaching a mobile tracker to the mobile part;
attaching the fixed part to the bone;
adjusting the position of the mobile part with respect to the fixed part.

According to an embodiment, the fixed part comprises a bone fixation and the step of attaching the fixed part to the bone comprises the step of attaching the bone fixation to the bone and the step of attaching the fixed part to the bone fixation.

The step of attaching the fixed tracker to the fixed part thus preferably consists in attaching the fixed tracker to the bone fixation.

DETAILED DESCRIPTION OF A PREFERRED EMBODIMENT

Navigated Cutting Block

Figure 1:
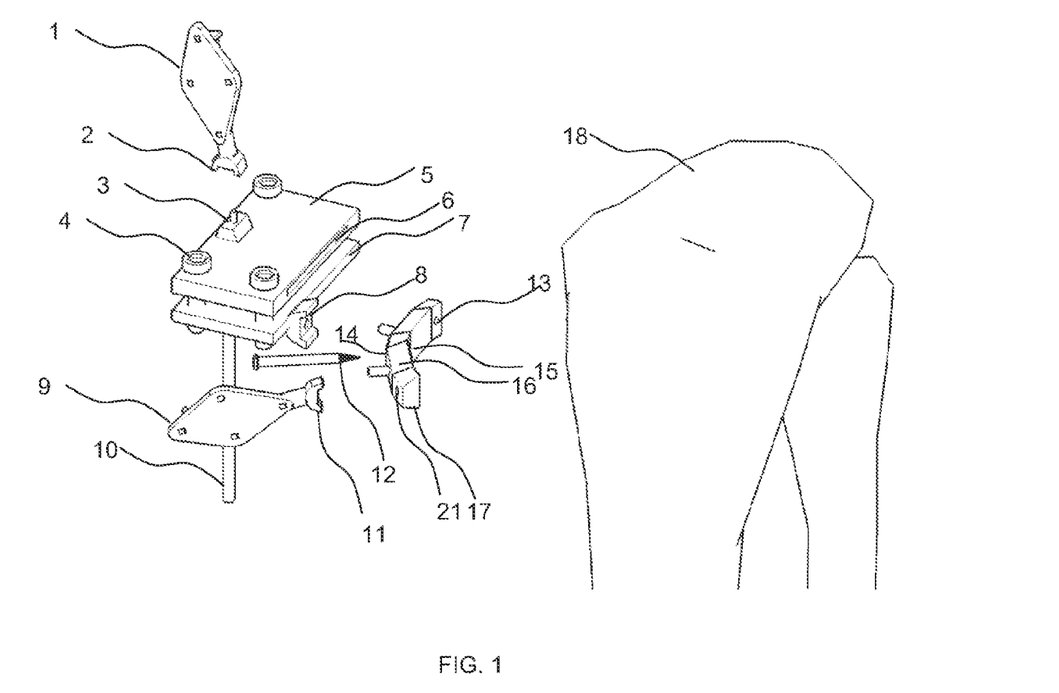
FIG. 1 is a perspective view showing the different parts of the device of the invention

Referring to FIG. 1, the device of the invention is a navigated cutting block that is described as follows.

The device of the invention comprises a fixed part 7 which is rigidly attached to the bone 18. In one preferred embodiment, a bone fixation 17 is rigidly fixed to the bone 18 by screws or pins 12 inside some dedicated holes 13, 21, 14. The bone fixation is as small as possible and it is rigid enough to support the strengths applied by a saw in a cutting block that will be mounted on it. Screws 12 have typically a diameter between 3 and 6 mm. At least two screws are used but the user can check the rigidity of the fixation and add one or more screws in addition if necessary. In order to reinforce the mechanical stability, the screws can have two threads like the ones that are commonly used for fixing plates in traumatology; one thread is adapted to the bone and a second thread close to the screw head is used to lock the screw to the bone fixation. Such mechanism can include the possibility to use variable angles of the screws inside the bone fixation, for instance with a ball-and-socket joint constituted by an expandable ring. The fixed part 7 is attached to the bone fixation 17 by a mechanism 8, 15 allowing the surgeon to assemble and disassemble it from the bone fixation during the surgical procedure. The mechanism 8 guaranties a strong fixation between the fixed part 7 and the bone fixation 17 but with fast assembling or disassembling, by a clip mechanism for instance or preferably by one locking screw. This functionality is useful for the surgeon because the cutting block is used for a very few steps of the surgery, and it is cumbersome enough to restrict some movements or positions of the knee, or bother the surgeon when he manipulates some surgical instruments around the knee. Therefore, for every step where the cutting block is not necessary, the surgeon is allowed to remove it. It makes it possible to use the conventional incision size and minimally-invasive surgery protocols. The mechanism is represented here by a small male part 15 and a small female part 8 that clips to it but this mechanism can be larger and optionally a fixation screw can be added to create a rigid fixation.

The device of the invention also comprises a mobile part 5 that is mobile with respect to the fixed part 7. A cutting slot 6 is inserted into the mobile part so that the surgeon can insert a saw to perform the cut.

In one preferred embodiment, the mobile part 5 is adjustable by 3 screws 4 with the help of a screwdriver. Each turn of a given screw makes the mobile part 5 move in a dedicated direction. The screws 4 are adjusted manually or automatically until a target position has been reached using the control of the navigation system. This design is specifically intended to be a parallel architecture made of three adjustments, by opposition to serial mechanisms. The parallel architecture has the advantage to be very stiff so that the global relationship between the bone fixation and the cutting block is stable when an oscillating saw is inserted in the cutting block. In a preferred embodiment, the parallel architecture is implemented by three screws 4 that are external to the cutting guide with a conventional thread in the mobile part and a pure rotating thread with no translation in the fixed part such that the screw end is fixed with respect to the fixed part. This solution requires that the cutting block is located between the three screws, which limits its width. In a second preferred embodiment, the screw end is passing through a thread of the fixed part and the screw head has a pure rotation with no translation with respect to the mobile part. The latter solution makes it easier to design a compact cutting guide that can be fixed or detachable with respect to the mobile part. Both designs can also be combined with some screws passing through the fixed part and other screws passing through the mobile part, which offers a tradeoff for compact cutting guide with enough guiding surface for the saw blade. For any of the designs mentioned above, the distances between the screws attachment on the fixed or mobile part does not remain constant; it is therefore necessary to have mechanisms in which some portions of at least two screws 4 can slide in a plane roughly parallel to the cutting guide. This can be implemented by creating a small housing of a few millimeters for a miniature ball-and-socket joint that is linked to the screw. It can be also implemented using flexure of plastic components.

If the cutting guide is not stable enough, for instance because of poor bone quality, it is also possible to add pins or screws on the cutting block when it is in its final position.

In this design, the range of motion of the mobile part 5 is limited to a few millimeters and degrees which can prevent to reach the desired position of the cutting slot if the bone fixation is not positioned correctly. In our invention, it is proposed to include a template (described below referring to FIG. 4) to help the surgeon positioning the bone fixation in a position called rough position, so that the adjustment ranges of the mobile part allows the surgeon to reach the desired position from the rough position when the screws are in their middle range.

In another embodiment (not illustrated), the mobile part is made of two detachable parts. It comprises a mechanism with screws 4 to move the block with respect to the fixed part and a separate cutting guide that can slide on the mobile mechanism. This design has the advantage that the absence of the cutting block makes easier the access to the manipulating screws 4 and also that the cutting block can slide until it reaches contact with the bone surface in order to improve stability during the cutting phase when a saw blade is inserted into the cutting guide.

In another embodiment (not illustrated), the mobile part is adjustable by series of translations, rotations and ball-and-socket articulations. Typically two rotations and one translation are necessary to adjust the cutting plane position under control of the navigation system. A mechanism allows the surgeon to unlock one or several degrees of freedom of the mobile part position, adjust the mobile part to the desired position, and then lock the position.

The cutting block is defined as the block composed of the fixed part 7, the mobile part 5, and the mechanism that links the fixed and mobile parts such as screws 4 or rotations and translations. The cutting block is the element that can be assembled and disassembled from the bone fixation 17.

A mobile tracker 1 is rigidly attached on the mobile part 5 so that the mobile part, and especially the cutting slot 6, is tracked by the navigation system. The cutting slot 6 determines a unique cutting plane. In one preferred embodiment, the tracker 1 can be assembled and disassembled from the mobile part 5 by a reproducible fixation, represented here by a male part 3 and a female part 2.

A fixed tracker 9 is rigidly attached on the bone fixation 17 so that the bone 18 is tracked by the navigation system. In one preferred embodiment, the tracker 9 can be assembled and disassembled from the bone fixation 17 by a reproducible fixation represented here by a male part 16 and a female part 11.

Figure 2:
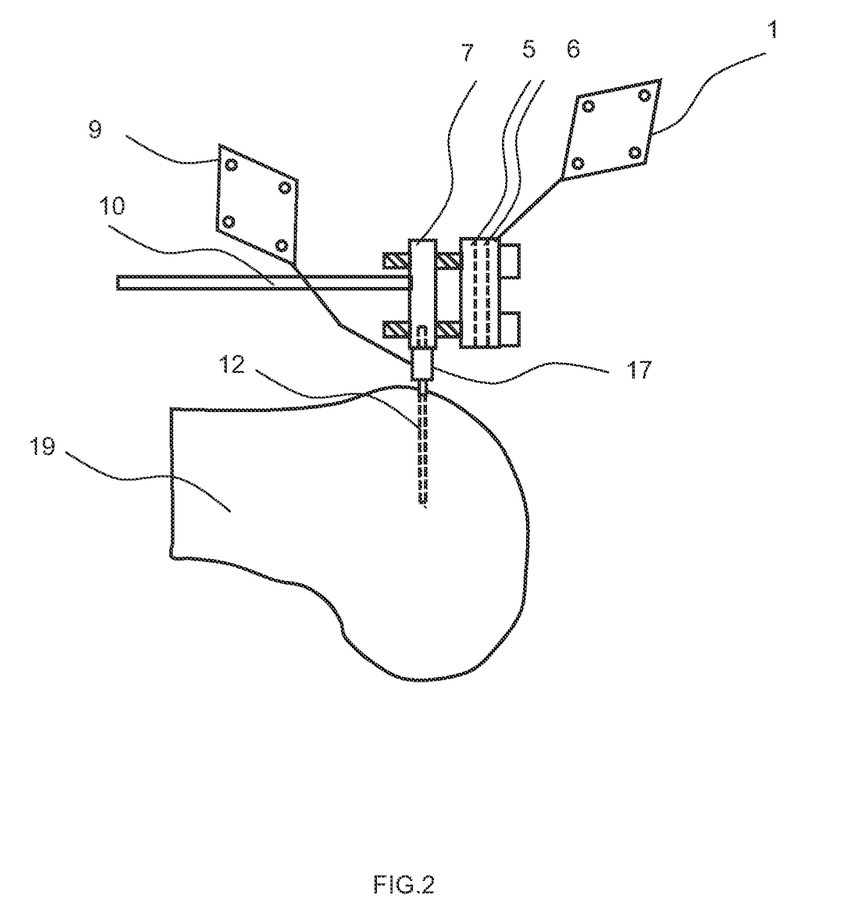
FIG. 2 is an elevational view of the device of the invention fixed on the femur, for the purpose of navigating the femoral distal cut.

FIG. 2 shows the use of the device of the invention on the femur 19. The fixed part 7 is attached to the bone fixation 17 thanks to the reproducible fixation described above. In this context, the goal of the device of the invention is to adjust the cutting plane of the femoral distal cut, determined by the plane of the cutting slot 6.

Figure 3:
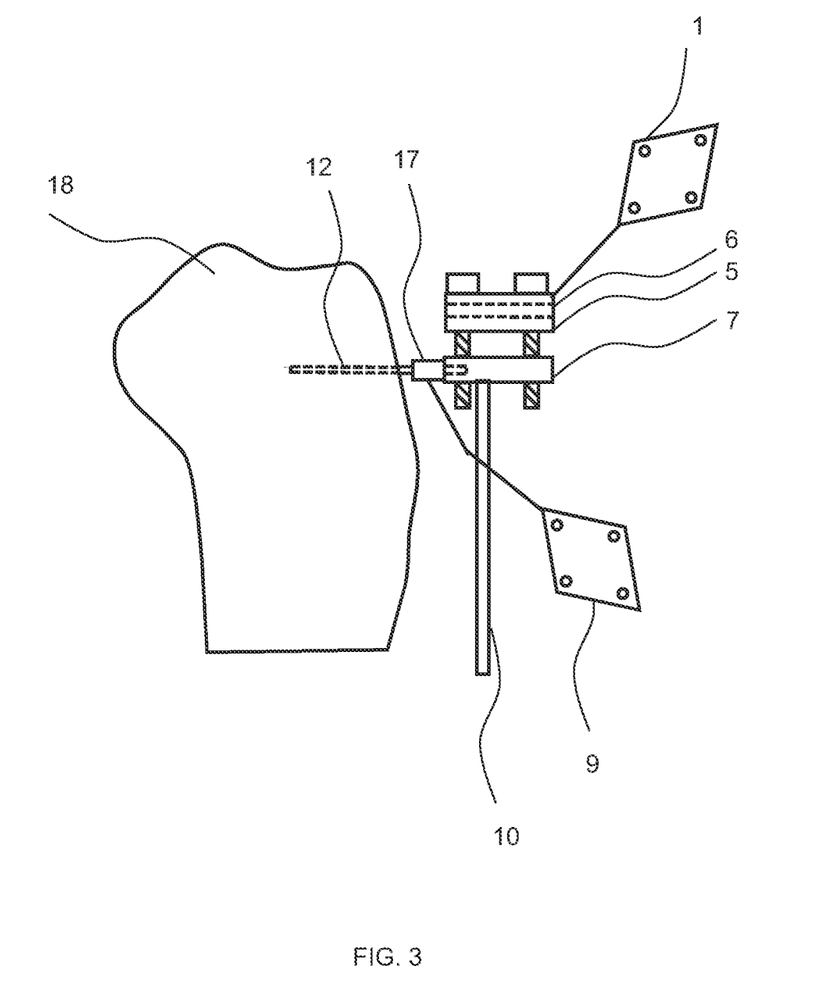
FIG. 3 is an elevational view of the device of the invention fixed on the tibia, for the purpose of navigating the tibial cut.

FIG. 3 shows the use of the device of the invention on the tibia 18. The fixed part 7 is attached to the bone fixation 17 thanks to the reproducible fixation described above. In this context, the goal of the device of the invention is to adjust the cutting plane of the tibial cut, determined by the plane of the cutting slot 6.

In another embodiment (not shown), the fixed part is directly fixed to the bone by screws or pins without any mechanism, removing the possibility to disassemble and reassemble the cutting block during the surgical procedure.

This design has the advantage of being simple and compact but it has the drawback of being cumbersome if the surgeon uses it on both femur and tibia at the same time. It is particularly suited if the surgeon uses navigation first on the tibia and then on the femur in two independent steps. In this case, the fixed tracker is attached to the fixed part.

Figure 4:
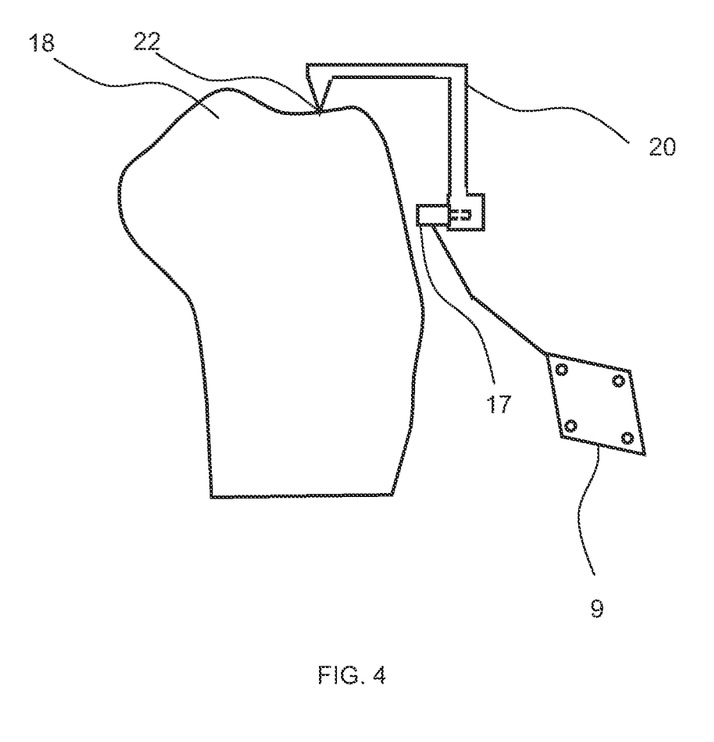
FIG. 4 is an elevational view of the template that helps the surgeon to place the bone fixation in a rough position.

Referring to FIG. 4, in order to help the surgeon positioning the device of the invention with respect to the bone in the rough position, a template 20 is attached to the bone fixation 17 and has some contact points 22 with anatomical landmarks for average conditions. Before positioning the bone fixation 17, the user must check that the template landmarks are in contact with the anatomical landmarks within a reasonable tolerance that makes it easy and fast to position, such as 10 mm and 15°. In the design where the fixed part is directly fixed to the bone, without any intermediary bone fixation, the template is attached to the fixed part instead of the bone fixation. The more the range of the adjustment mechanism of the mobile part is large, the less the rough position requires being accurate.

As shown on FIGS. 1 to 3, a rod 10 on the bottom of the fixed part 7 helps the surgeon to first manipulate the device of the invention, and second to help the surgeon to reach the rough position in addition to the template. Indeed the rod 10 is designed so that its axis is supposed to be parallel to the mechanical axis (tibia or femur) once the cutting block is in the rough position.

Typically on the tibia, the template is made of one contact point on the medial or lateral plateau with the rod set parallel to the tibial axis. Typically on the femur, the template is made of one contact point on the medial or lateral distal condyle with the rod set parallel to the femoral axis.

Surgical Procedure Flow Diagram

In one example of use of the device of the invention, the surgical procedure flow diagram that uses the device of the invention is the following:

A—Tibia Preparation:
1. Bone Fixation on the tibia. Referring to FIG. 3, the bone fixation 17 is rigidly fixed on the tibia 18 by pins or screws, with the help of a template 20.
2. Tracker fixation on the tibia. The tracker 9 is rigidly attached on the bone fixation 17. Thanks to the rigid fixation of the bone fixation on the tibia, and thanks to the rigid fixation of the tracker 9 on the bone fixation 17, the tracker 9 is then rigidly attached to the tibia 18. The navigation system can track the position and orientation of the tibia.
3. Tibial Acquisition. The user is instructed to acquire some precise anatomical data that are necessary for navigating the tibial cut such as tibia center, tibia height reference point, and ankle center defined by external and internal malleoli. The definitions and the methods to acquire those anatomical points are independent of the invention.
4. Tibial Cutting Block fixation. The cutting block is mounted on the bone fixation 17 and the tracker 1 is rigidly linked to the cutting slot 6 of the mobile part 5.

B—Tibial Cut Steps:
1. Tibial Cut navigation. The user can control and adjust the position of the tibial cut with respect to the tibial anatomical data using the navigation system. The tibial cut is performed when the slot 6 is in the target position selected by the surgeon.
2. Tibial Cutting Block removal. The user can remove the tibial cutting block in order to let the maximum of space available for the next surgical steps. Only the bone fixation 17 remains on the tibia 18. In order to control the global leg alignment and knee balancing in further steps, the mobile tracker is attached to the fixation 17 by the mechanism mentioned above. Optionally, the bone fixation 17 can be removed totally if those further steps are not required by the surgeon.

C—Femur Preparation
1. Bone Fixation on the femur. Referring to FIG. 2, the bone fixation 17 is rigidly fixed on the femur 19 by pins or screws.
2. Tracker fixation on the femur. The tracker 9 is rigidly attached on the bone fixation 17. Thanks to the rigid fixation of the bone fixation 17 on the femur 19, and thanks to the rigid fixation of the tracker 9 on the bone fixation 17, the tracker 9 is then rigidly attached to the femur 19. The navigation system can track the position and orientation of the femur.
3. Femoral Acquisition. The user is instructed to acquire some precise anatomical data that are necessary for navigating the femoral distal cut such as femoral center, posterior condyles, distal condyles, anterior cortex by digitization and hip center by pivoting the leg. The definitions and the methods to acquire those anatomical points are independent of the Invention.
4. Femoral Cutting Block fixation. The cutting block is mounted on the bone fixation 17 and the tracker 1 is rigidly linked to the cutting slot 6 of the mobile part 5.

D—Femoral Distal Cut Steps:
1. Femoral Distal Cut navigation. The user can control and adjust the position of the femoral distal cut with respect to the femoral anatomical data using the navigation system. The femoral cut is performed when the slot 6 is in the target position selected by the surgeon.
3. Femoral Cutting Block removal. The user can remove the femoral cutting block in order to let the maximum of space available for the next surgical steps. Only the bone fixation 17 remains on the femur 19. In order to control the global leg alignment and knee balancing in further steps, the mobile tracker is attached to the fixation 17 by the mechanism mentioned above. Optionally, the bone fixation 17 can be removed totally if those further steps are not required by the surgeon.

E—Others Femoral Cut:
1. 4-in-1 cutting block navigation. Thanks to the femoral tracker that stays in place once the cutting block is removed, one can still navigate a 4-in-1 cutting block. The 4-in-1 cutting block is defined as an instrument with four cutting slots for the anterior cut, the posterior cut and two chamfers. A tracker is attached to the 4-in-1 cutting block so that the navigation system can compute the position of the 4-in-1 cuts with respect to the femoral referential. However, the fixation pins of the femoral trackers may interfere with the fixation of the 4-in-1 cutting block. To prevent this problem, a first possibility is to design the 4-in-1 fixation and the femoral trackers pins such that they do not have risk to intersect. A second possibility is to use the navigation system to indicate where those pins are located in the bone and to make sure that the axis of the holes included in the 4-in-1 cutting block will not intersect those pins.

The groups of steps A to E can be switched in other orders, provided that Tibia Preparation (A) is done before Tibial Cut (B) and provided that Femoral Preparation (C) is done before femoral cuts (D) (E). Examples of protocols:
1. A,B,C,D,E
2. C,D,E,A,B
3. A,C,B,D,E
4. C,E,A,B,D The cutting blocks can take various forms and the femoral cutting block can be for instance a device that contains five slots for all cuts, and also cuts for the notch.

Advantages of the Invention

The advantage of the invention is to avoid additional fixation to the bone for the use of navigation tracker, compared to the conventional method of navigation system where the tracker is attached to the bone by pins or screws, in addition to the pins or screws used to attach the cutting blocks to the bone.

The invention claimed is:

1. A surgical navigation device, for the purpose of adjusting a cutting plane to a desired position with respect to a bone of a patient, the device comprising:
   a bone fixation device constructed to be rigidly attached to the bone, the bone fixation device comprising a first fixation means for rigidly attaching a tracker to the bone fixation device and a second fixation means for releasably attaching a fixed part to the bone fixation device;
   a template constructed to be releasably attached to the bone fixation device, wherein the template comprises landmarks corresponding to anatomical landmarks of the bone for rough positioning of the bone fixation device relative to the bone, wherein the template is configured to be removed from the bone fixation device before the fixed part is attached to the bone fixation device;
   the fixed part constructed to be releasably attached to the bone fixation device via the second fixation means;
   a mobile part that is coupled to the fixed part and adjustable with respect to the fixed part, the mobile part including third fixation means for rigidly attaching a tracker to the mobile part, and including a cutting slot in which a saw blade can be inserted to perform cutting;
   a fixed tracker that is constructed to be rigidly attached to the bone fixation device via the first fixation means; and
   a mobile tracker that is constructed to be attached to the mobile part via the third fixation means,
   wherein the mobile and fixed parts are constructed to be removed as a unit from the bone fixation device when the bone fixation device is attached to the bone by detaching the fixed part from the second fixation means, and
   wherein the bone fixation device and the fixed part together support the mobile part in position with respect to the bone during a cutting operation by the saw blade inserted into the cutting slot.

2. The device of claim 1, wherein the mobile part is adjusted with respect to the fixed part using a parallel architecture made of three screws.

3. The device of claim 1, wherein the fixed part comprises a rod for manipulating and aligning the device.

4. The device of claim 1, wherein the bone fixation device is constructed to be rigidly attached to a portion of the bone that will remain after the bone is cut.

5. A method for adjusting a cutting plane of a surgical device to a desired position with respect to a bone of a patient, the device comprising a bone fixation device to be rigidly attached to the bone, a fixed part to be releasably attached to the bone fixation device, and a mobile part that is coupled to the fixed part and adjustable with respect to the fixed part, and including a cutting slot in which a saw blade can be inserted to perform cutting, the mobile and fixed parts being removable as a unit from the bone fixation device when the bone fixation device is attached to the bone, said method comprising the following steps:
   attaching a fixed tracker to the bone fixation device;
   attaching a mobile tracker to the mobile part;
   attaching the bone fixation device to the bone;
   attaching the fixed part to the bone fixation device;
   adjusting the position of the mobile part with respect to the fixed part;
   cutting the bone by inserting the saw blade into the cutting slot; and
   after the cutting the bone, removing the mobile and fixed parts as a unit from the bone fixation device so as to leave the bone fixation device attached to the bone,
   wherein before attaching the bone fixation device to the bone, a template for rough positioning of the bone fixation device is attached to the bone fixation device, the template comprising landmarks corresponding to anatomical landmarks of the bone, the template being positioned on the bone such that the landmarks of the template are in contact with the anatomical landmarks of the bon;
   wherein the template is removed from the bone fixation device before the fixed part is attached to the bone fixation device.

6. The method of claim 5, wherein the mobile part is adjusted with respect to the fixed part using a parallel architecture made of three screws.

7. The method of claim 5, wherein the bone fixation device is constructed to be rigidly attached to a portion of the bone that will remain after the bone is cut.

* * * * *

UNITED STATES PATENT AND TRADEMARK OFFICE
CERTIFICATE OF CORRECTION

PATENT NO. : 9,655,628 B2
APPLICATION NO. : 13/318815
DATED : May 23, 2017
INVENTOR(S) : Anthony Boyer and Stephane Lavallee It is certified that error appears in the above-identified patent and that said Letters Patent is hereby corrected as shown below:

In the Claims

Column 8, Claim 5, Line 38, please delete "bon;" and insert --bone,--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*